United States Patent
Bhadra et al.

(10) Patent No.: US 9,387,322 B2
(45) Date of Patent: Jul. 12, 2016

(54) THERAPY DELIVERY DEVICES AND METHODS FOR NON-DAMAGING NEURAL TISSUE CONDUCTION BLOCK

(71) Applicant: Case Western Reserve University, Cleveland, OH (US)

(72) Inventors: Niloy Bhadra, Cleveland Heights, OH (US); Kevin L. Kilgore, Avon Lake, OH (US); Narendra Bhadra, Chesterland, OH (US); Jesse Wainright, Willoughby Hills, OH (US); Tina Vrabec, Willoughby Hills, OH (US); Manfred Franke, South Euclid, OH (US)

(73) Assignee: Case Western Reserve University, Cleveland, OH (US)

( * ) Notice: Subject to any disclaimer, the term of this patent is extended or adjusted under 35 U.S.C. 154(b) by 0 days.

(21) Appl. No.: 14/408,017

(22) PCT Filed: Jun. 14, 2013

(86) PCT No.: PCT/US2013/045859
§ 371 (c)(1),
(2) Date: Dec. 15, 2014

(87) PCT Pub. No.: WO2013/188753
PCT Pub. Date: Dec. 19, 2013

(65) Prior Publication Data
US 2015/0174397 A1    Jun. 25, 2015

Related U.S. Application Data

(60) Provisional application No. 61/660,383, filed on Jun. 15, 2012, provisional application No. 61/821,862, filed on May 10, 2013.

(51) Int. Cl.
*A61N 1/00* (2006.01)
*A61N 1/05* (2006.01)
*A61N 1/06* (2006.01)
*A61N 1/36* (2006.01)

(52) U.S. Cl.
CPC ............. *A61N 1/0556* (2013.01); *A61N 1/06* (2013.01); *A61N 1/36064* (2013.01); *A61N 1/36067* (2013.01); *A61N 1/36071* (2013.01)

(58) Field of Classification Search
USPC .......................................................... 607/50
See application file for complete search history.

(56) References Cited

U.S. PATENT DOCUMENTS

2003/0040785 A1    2/2003    Maschino et al.
2011/0021943 A1    1/2011    Lacour et al.
(Continued)

FOREIGN PATENT DOCUMENTS

WO         2010042750 A2    4/2010

OTHER PUBLICATIONS

International Search Report for PCT/US2013/045859, mailed Oct. 9, 2013, pp. 1-5.

*Primary Examiner* — Nicole F Lavert
(74) *Attorney, Agent, or Firm* — Tarolli, Sundheim, Covell & Tummino LLP

(57) ABSTRACT

Devices and methods for blocking signal transmission through neural tissue. One step of a method includes placing a therapy delivery device into electrical communication with the neural tissue. The therapy delivery device includes an electrode contact having a high charge capacity material. A multi-phase direct current (DC) can be applied to the neural tissue without damaging the neural tissue. The multi-phase DC includes a cathodic DC phase and anodic DC phase that collectively produce a neural block and reduce the charge delivered by the therapy delivery device. The DC delivery can be combined with high frequency alternating current (HFAC) block to produce a system that provides effective, safe, long term block without inducing an onset response.

8 Claims, 15 Drawing Sheets

(56) References Cited

U.S. PATENT DOCUMENTS

| | | | |
|---|---|---|---|
| 2011/0077660 A1* | 3/2011 | Janik | A61N 1/0553 606/129 |
| 2011/0160798 A1 | 6/2011 | Ackermann, Jr. et al. | |
| 2011/0190849 A1* | 8/2011 | Faltys | A61N 1/36053 607/50 |

* cited by examiner

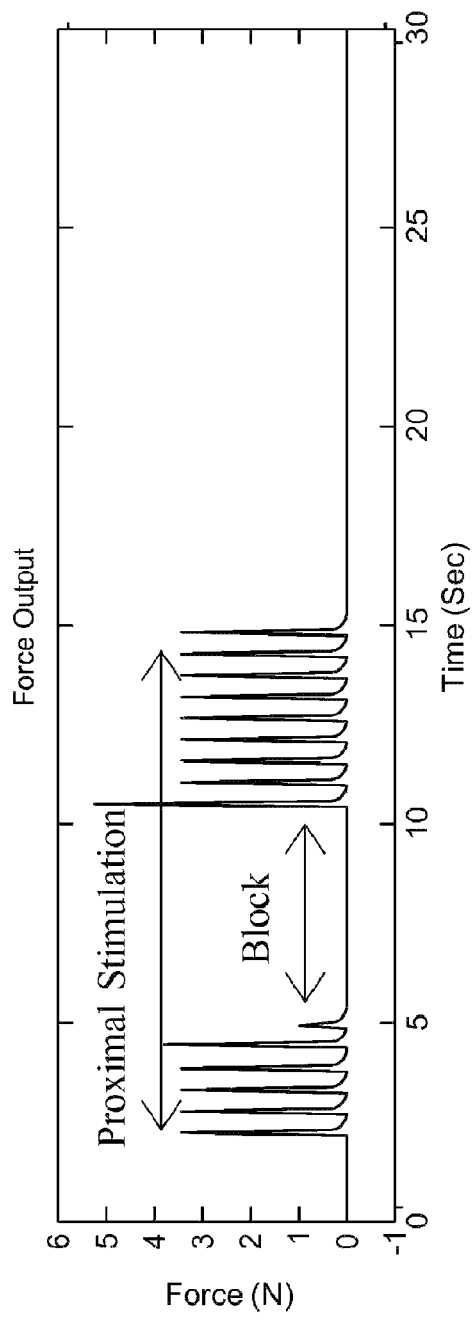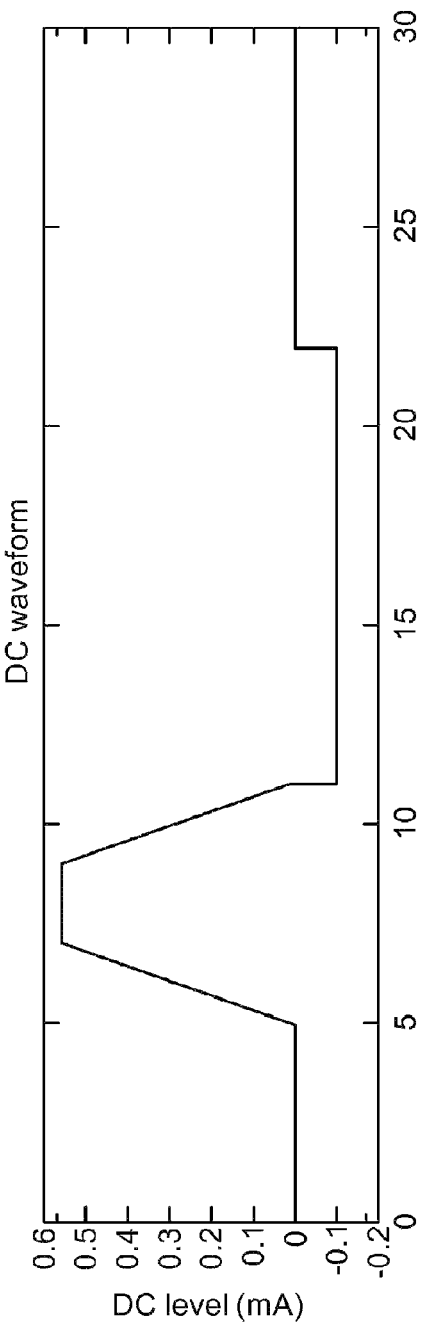

THERAPY DELIVERY DEVICES AND METHODS FOR NON-DAMAGING NEURAL TISSUE CONDUCTION BLOCK

RELATED APPLICATIONS

This application claims priority from U.S. Provisional Patent Application Ser. Nos. 61/660,383, filed Jun. 15, 2012, and 61/821,862, filed May 10, 2013. The entirety of each of the aforementioned applications is hereby incorporated by reference for all purposes.

TECHNICAL FIELD

The present invention generally relates to systems, devices and methods for blocking signal transmission through neural tissue, such as a nerve, and more particularly to therapy delivery systems, devices, and methods for using direct current to block neural signal transmission without damaging the neural tissue.

BACKGROUND

Many neurological diseases are characterized by undesirable neural activity resulting in severe symptoms. Such diseases include spasticity, movement disorders, and chronic pain of peripheral origin. A localized, reversible, electrical nerve conduction block would be an attractive way of addressing these conditions.

High Frequency Alternating Current (HFAC) waveforms have been shown to provide a very localized, immediate, complete, and reversible conduction block for motor and sensory nerve fibers in acute animal preparations without indications of nerve damage. However, HFAC produces a transient neural activity when turned on. This effect has been termed the "onset response." The onset response can take many seconds to diminish and cease. If an HFAC nerve block were applied to a mixed nerve, the onset response could produce a painful sensation coupled with muscle contractions. The onset response has prevented the practical use of HFAC block for spasticity control and other applications. Efforts have been made to shorten the HFAC so that it generally lasts less than two seconds. These methods include the use of large HFAC amplitudes, higher frequencies (>20 kHz), and various electrode configurations. However, the initial portion of the onset response, lasting one to two seconds, is a component of HFAC block that has not been eliminated through modification of the waveform or electrode design alone.

A second form of electric nerve block can be achieved with direct currents (DC). In addition to other manipulations, slowly ramping the DC amplitude over the course of a few seconds can produce a DC block without evoking action potentials. This allows for DC nerve block without an onset response. However, application of DC waveforms results in nerve damage due probably to the creation of free radicals at the electrode-electrolyte interface after the charge injection capacity of the interface is exhausted and the voltage across the interface leaves the water-window. The water-window is the specific voltage range for each electrode-electrolyte interface that is limited by the activation energy, or applied external voltage, necessary to produce molecular oxygen and hydrogen. An advantage of a DC block is that it can be achieved without causing an onset response by gradually ramping the current amplitude. This is an effect that has not been achieved with HFAC block waveforms.

As such, a need exists for a better method of blocking neural conduction.

SUMMARY

In general, the present invention relates to devices and methods for blocking signal transmission through a neural tissue.

In an embodiment, the present invention provides a therapy delivery device comprising an electrode contact comprising a high-charge capacity material. The electrode contact has a geometric surface area of at least about 1 $mm^2$.

In another embodiment, the present invention provides a method of blocking signal transmission through neural tissue by placing a therapy delivery device into electrical communication with the neural tissue. The therapy delivery device comprises an electrode contact comprising a high charge capacity material. The method further comprises applying current to the neural tissue to block signal transmission through the tissue without damaging the tissue.

In certain embodiments, a multi-phase DC current is applied to the neural tissue. Such a multi-phase DC current comprises a phase of a first polarity configured to block signal transmission through the neural tissue and a phase of a second, opposite polarity configured to reduce the net charge transmitted by the therapy delivery device. Preferably, the subsequent current delivered has an equal and opposite charge in opposite polarity to the first current delivered resulting in a zero net charge delivered. In certain embodiments, the multi-phase DC current comprises a cathodic phase configured to block signal transmission through the neural tissue and an anodic phase configured to reduce the net charge transmitted by the therapy delivery device. In other embodiments, the anodic phase is configured to block signal transmission and the cathodic phase is configured to reduce the net charge. In certain embodiments, applying the cathodic DC phase comprises applying a DC having a first DC amplitude, increasing the first DC amplitude to a second DC amplitude over a first period of time insufficient to block neural signal transmission, maintaining the second DC amplitude for a second period of time sufficient to block neural signal transmission, and decreasing the second DC amplitude to a third DC amplitude to reduce the net charge delivered to the neural tissue. The net charge can be reduced to substantially zero. In certain embodiments, delivering the first and second DC amplitudes over the first and second periods of time substantially prevents axonal firing. The duration of the recharge phase can be about equal to or greater than the duration of the blocking phase. In the case of a plurality of electrode contacts, the multi-phase DC can be continuously cycled through each of the electrode contacts such that a continuous block in neural signal transmission is achieved.

In other embodiments, a multi-phase DC is applied to the neural tissue, which includes a cathodic DC phase and an anodic DC phase that are collectively configured to block neural signal transmission and reduce the charge transmitted by the therapy delivery device. The method further includes applying a HFAC to the neural tissue before, during or after application of the multi-phase DC. The HFAC has a HFAC amplitude, a HFAC frequency, and a HFAC current. The HFAC is configured to block neural signal transmission. The combination of the multi-phase DC and the HFAC and the order in which the multi-phase DC and the HFAC are applied reduce an onset activity in the neural tissue associated with blocking the signal transmission through the neural tissue while also preventing neural damage.

BRIEF DESCRIPTION OF THE DRAWINGS

The foregoing and other features of the present disclosure will become apparent to those of skill in the art to which the present disclosure relates upon reading the following description with reference to the accompanying drawings in which:

FIG. 3 is a schematic illustration of a DC plus HFAC no-onset blocking system.

FIG. 4 is a graph illustrating the effect of electric nerve block waveforms on evoked gastrocnemius muscle forces.

FIG. 10 is an illustrative DC block trial showing that the twitches elicited by proximal stimulation are blocked during the blocking phase of a trapezoidal waveform according to an embodiment of the present invention.

DETAILED DESCRIPTION

Figure 1A:
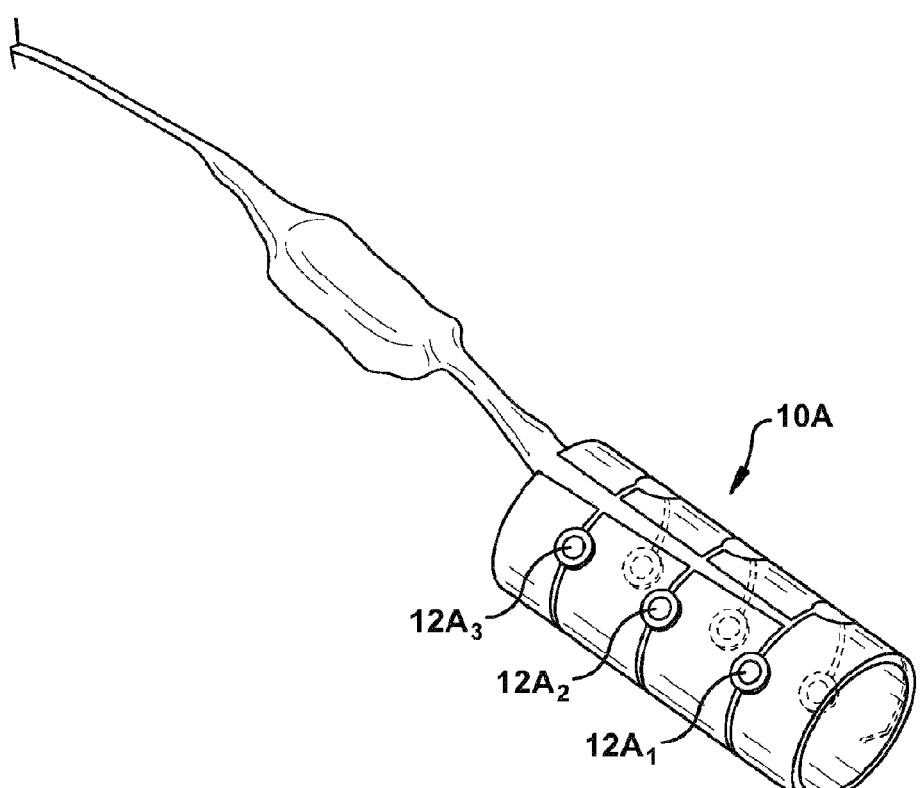
FIG. 1A is an exemplary therapy delivery device according to an embodiment of the present invention.

In the context of the present invention, the term "patient" refers to a mammal such as a human being. Also, as used herein, the term "high frequency" with reference to alternating current (e.g. HFAC) refers to frequencies above approximately one kiloHertz (kHz) such as, for example, about 5 to about 50 kHz. The term "electrical communication" refers to the ability of an electric field to be transferred to, or having a neuromodulatory effect (e.g. blocking neural signal transmission) within and/or one at least one neural tissue including a nerve, neuron, or other type of nervous system tissue of a patient. A therapy delivery device, described in more detail herein, can be positioned directly on the neural tissue or near, but not in direct contact with, the neural tissue. The term "electrode contact comprising a high charge capacity material" refers to an electrode contact that delivers a charge or has a "Q value" of above about 100 microcoulombs (μC) without damaging the neural tissue. As is known in the art, the Q value of an electrode contact is the charge capacity of the electrode contact and is effectively the total amount of charge that can be delivered through an electrode contact before the electrode contact starts to transition to irreversible chemical reactions. The primary irreversible reactions that occur are oxygen evolution or hydrogen evolution depending on the polarity of the charge being delivered. Other irreversible reactions can occur as well such as dissolution of the electrode material. The disclosure herein refers to the term "geometric surface area" of an electrode contact. This refers to two-dimensional surface area of the electrode contact such as the smooth surface on one side of the electrode contact as calculated by the length times the width of the two-dimensional outer surface of the electrode contact. The "effective or true surface area" of an electrode contact is inferred from the area within the curve of a cyclic voltammogram of the electrode contact. Further, as used herein with respect to a described component, the terms "a," "an," and "the" include at least one or more of the described component including a plurality of the described component unless otherwise indicated. Further, the term "or" includes "and/or" unless otherwise indicated.

In general, the present invention relates to therapy delivery devices and methods for blocking signal transmission through a neural tissue. The therapy delivery devices comprise an electrode contact comprising a high charge capacity material. As stated above, the electrode contact has a Q value of above about 100 μC. In certain embodiments, the electrode contact has a Q value of between about 1 and about 100 millicoulombs (mC). In preferred embodiments, the Q value is on the order of 10 mC. In certain embodiments, the high charge capacity material has a charge injection capacity (the charge density that safely can be delivered through the material) of about 1 to about 5 mC/cm$^2$. In comparison, polished platinum, a non-high charge capacity material, has a charge injection capacity of about 0.05 mC/cm$^2$. With an electrode contact comprising a high charge capacity material, the effective surface area of the electrode contact is increased by several orders of magnitude over the geometric surface area. More charge safely can be delivered to the neural tissue for longer periods of time compared to traditional stimulation electrodes such as those fabricated from platinum or stainless steel. As such, DC can be safely delivered through monopolar nerve cuff electrode contacts for durations as long as ten seconds without any nerve damage. Accordingly, the present invention provides systems, devices, and methods for providing an effective, reversible "no onset" neural block.

Figure 1B:
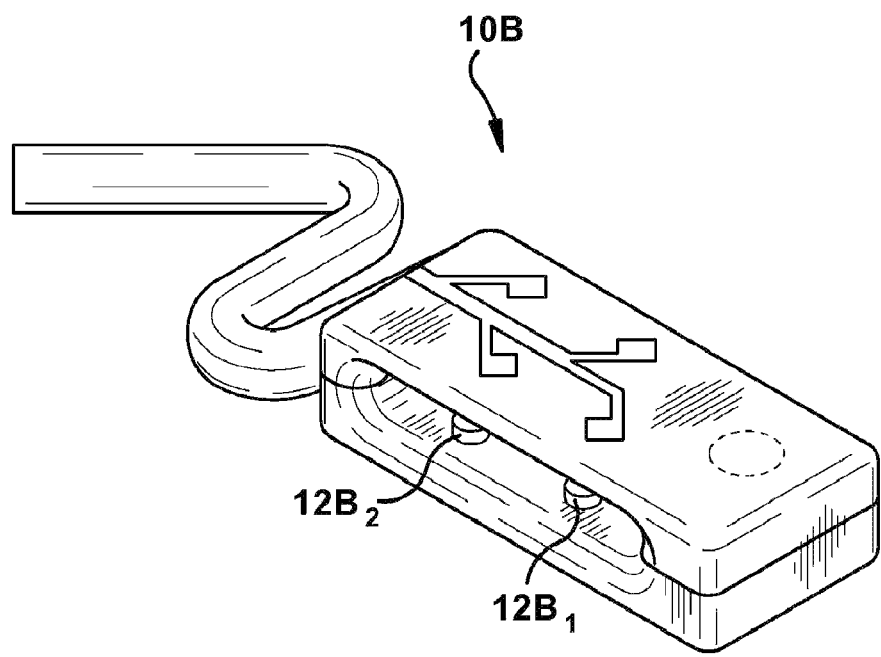
FIG. 1B is another exemplary therapy delivery device according to an embodiment of the present invention.

In particular with reference to FIGS. 1A and 1B, in an embodiment, the present invention provides a therapy delivery device 10 comprising an electrode contact 12. Electrode contact 12 comprises a high charge-capacity material. Electrode contact 12 has a geometric surface area of at least about 1 mm$^2$. In certain embodiments, the geometric surface area of electrode contact 12 is between about 3 mm$^2$ to about 9 mm$^2$. The electrode contact itself can be fabricated of a high charge capacity material. Alternatively, the electrode contact can comprise a base body at least partially coated with a high charge capacity material and preferably entirely coated with a high charge capacity material. Non-limiting examples of high charge capacity materials are platinum black, iridium oxide, titanium nitride, tantalum, poly(ethylenedioxythiophene) and suitable combinations thereof.

As shown in FIG. 1A, therapy delivery device 10A is a spiral nerve cuff electrode. As shown in FIG. 1B, therapy delivery device 10B is a flat interface nerve electrode. The nerve cuff electrode can take the form of a spiral cuff, a helical cuff, a flat interface nerve electrode, or other nerve cuff electrodes that place electrode contacts around the nerve or neural tissue. However, the therapy delivery device can have other configurations such as a mesh, a linear rod-shaped lead, paddle-style lead, or a disc contact electrode including a multi-disc contact electrode. The therapy delivery device can also be placed directly into the nerve or neural tissue, such as a penetrating intraneural electrode. As shown in FIG. 1A and FIG. 1B, therapy delivery devices 10A and 10B comprise a plurality of electrode contacts 12A and 12B, respectively, however the therapy delivery device can comprise less than a plurality of electrode contacts. Further, the therapy delivery device can comprise electrode contacts that do not comprise a high charge capacity material. The electrode contacts can either be monopolar or bipolar. In certain embodiments, the therapy delivery device comprises a plurality of multiple contiguous electrode contacts. In one example, the number of contiguous electrode contacts is four.

In general, the present invention also provides a method of blocking neural signal transmission. Such a method is distinct from activating neural signal transmission by applying short pulses (lasting microseconds) to the neural tissue. A method includes placing a therapy delivery device into electrical communication with the neural tissue. In certain embodiments, the therapy delivery device is applied directly to or in the neural tissue. In other embodiments, the therapy delivery device is located nearby, but not in direct contact with, the neural tissue. The therapy delivery device has an electrode contact comprising a high charge capacity material. The method further comprises applying current to the neural tissue to block neural signal transmission without damaging the neural tissue. In certain embodiments the current is direct current (DC). In other embodiments, the current is DC and HFAC. Preferably, the HFAC is applied after the DC. Because a high capacity charge material is used, the DC can be applied for longer periods of time than previous blocking DC waveforms without damaging the neural tissue or the electrode contact. For example, DC can be applied for at least about ten seconds. In certain embodiments, the DC is applied between about one second and about ten seconds. The DC can be applied between about ten seconds and about 600 seconds.

Figure 2:
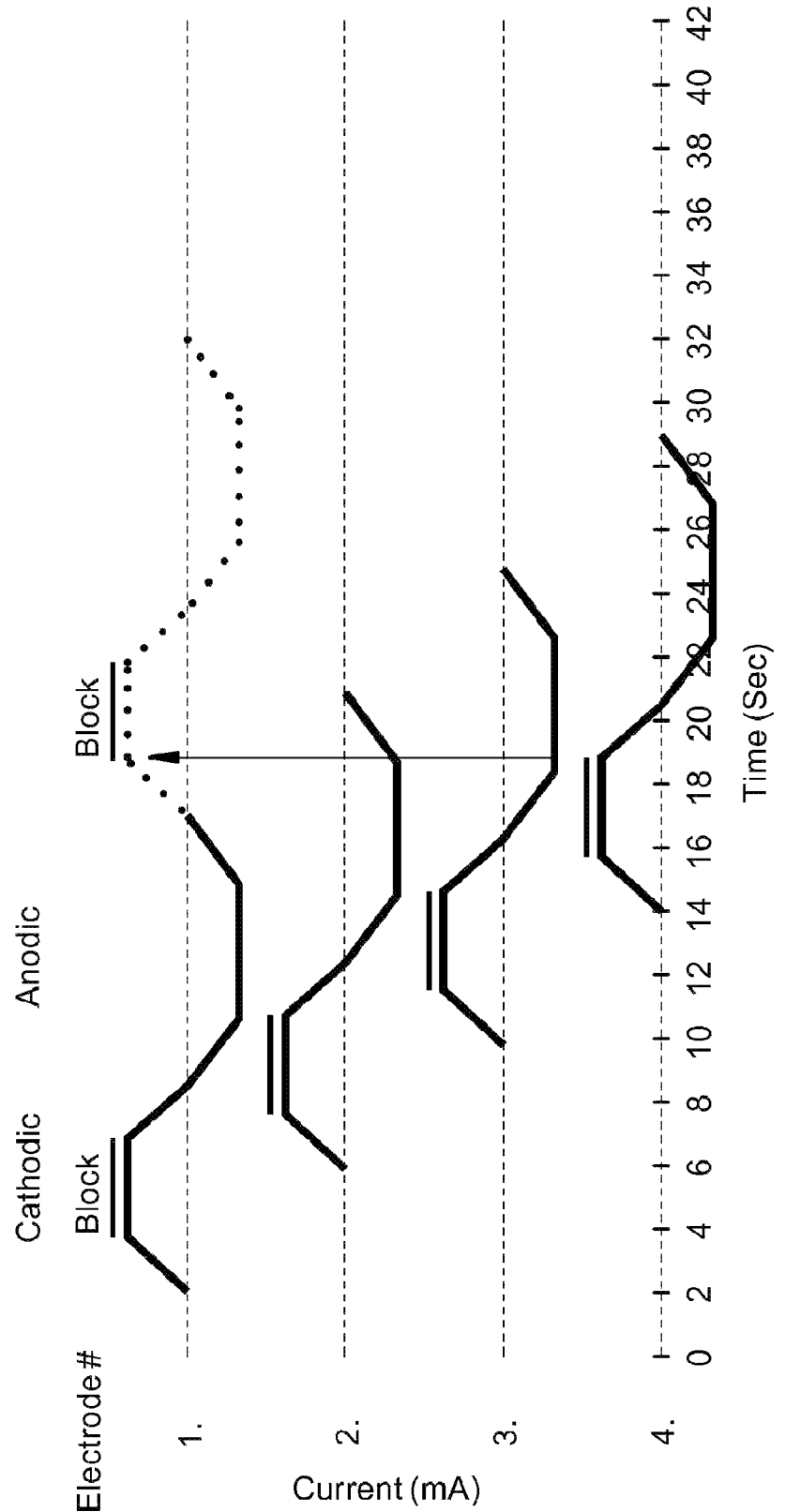
FIG. 2 is a schematic illustration depicting one example of a waveform and its application to four electrode contacts according to an embodiment of the present invention. The graph illustrates the current delivered by each electrode contact over time. The total time is approximately 60 seconds. Each plateau is approximately 5 seconds in length. The dotted lines for current indicates zero current for each the electrode contacts. The typical current for each plateau is 1-2 mA. The bars above the plateau indicate the period where the nerve is blocked by the respective electrode contact. At any period of time, at least one of the electrode contacts is blocking the nerve and thus it is continually blocked. The signal from each electrode contact keeps cycling through the same waveform (as indicated by the dotted line for electrode contact #1).

In certain embodiments, a multi-phase DC is applied to the neural tissue without causing damage to the neural tissue. The multi-phase DC can include a cathodic DC phase and a reciprocal anodic DC phase. The cathodic DC need not be applied first. As such, a multi-phase DC can be applied to the neural tissue including applying an anodic DC current and then a reciprocal cathodic DC current. One phase of the DC is configured to produce a complete, substantially complete, or even partial nerve block and the other phase is configured (e.g. by reversing the current) to reduce or balance a charge returned to the therapy delivery device. Exemplary multi-phase DC includes relatively slow current ramps that fail to produce an onset response in the neural tissue. For example, with reference to FIG. 2, a slow ramp of cathodal current, followed by a plateau, followed by a slow current ramp in the anodal direction can be applied to the neural tissue. The total net charge delivered by any of the electrode contacts can be equal to, or about equal to zero. Advantageously, delivery of a net zero charge is considerably safer to neural tissue. FIG. 2 illustrates waveforms having a substantially trapezoidal delivered by four electrode contacts ("1," "2," "3," and "4") of a therapy delivery device. Each of the cathodic and anodic DC phases begins and ends with a ramp, which prevents or substantially prevents any axonal firing. At the plateau of the cathodic DC phase, for example, there is complete neural block. As discussed above, the cathodic DC phase can cause neural block and, following this phase, the current is reversed (anodic DC phase) to balance the charge delivered by the therapy delivery device. The anodic recharge time can be about equal to, or moderately longer than the cathodic block time. Moreover, the cycles of cathodic block and anodic recharge can be applied to the neural tissue sequentially for prolonged periods of time without any neural damage. Again, the sequence of the DC phases can be reversed and the anodic DC phase may cause the neural block and the cathodic DC phase may balance the charge delivered by the therapy delivery device.

In some instances, the cathodic DC phase is conducted as follows. A DC having a first DC amplitude can be applied to the neural tissue. The first DC is then increased, over a first period of time, to a second DC amplitude. The DC having the first amplitude is insufficient to produce a partial or complete neural block. Next, the second DC amplitude is substantially maintained over a second period of time that is sufficient to produce a complete neural block. After the second period of time, the second DC amplitude is decreased to a third DC amplitude that is equal to, or about equal to, the first DC amplitude.

In an embodiment of a method, multiple contiguous electrode contacts can be placed into electrical communication with neural tissue. Such a configuration may be useful where neural conduction is not entirely blocked during the anodic or cathodic DC phase. In this case, the cathodic DC phase and the anodic DC phase can be continuously cycled amongst the electrode contacts so that there will be a continuous neural block without neural damage. In one example, and as shown in FIG. 2, the cathodic DC phase and the anodic DC phase can be continuously cycled amongst four contiguous monopolar electrode contacts so that there will be a continuous neural block without neural damage.

As already noted, another aspect of the present invention can include a method (as described above) that can be combined with HFAC delivery to reduce or eliminate an "onset response" in a subject. HFAC has been demonstrated to provide a safe, localized, reversible, electrical neural conduction block. HFAC, however, produces an onset response of short but intense burst of firing at the start of HFAC. Use of short durations of DC to block the neural conduction during this HFAC onset phase can eliminate the onset problem. Though DC can produce neural block, it can cause damage to neural tissue within a short period of time.

Advantageously, the methods described above can be combined with HFAC to eliminate the onset response without neural damage. For example, a multi-phase DC can be applied to the neural tissue. As discussed above, the cathodic DC phase can be configured to produce a neural block, the anodic DC phase can be configured to balance a charge delivered by the therapy delivery device, or vice versa. Before, during, or after application of the multi-phase DC, a HFAC can be applied to the neural tissue. The HFAC can have a HFAC amplitude, a HFAC frequency, and a HFAC current. The HFAC can be configured to produce a neural conduction block in the neural tissue. The combination of the multi-phase DC and the HFAC, and the order in which the multi-phase DC and the HFAC are applied, reduce an onset activity in the neural tissue associated with producing the conduction neural block while also preventing neuronal damage.

In certain embodiments, a "pre-charge" pulse is applied to the neural tissue. In particular, a DC having a first polarity is applied to the neural tissue and then a DC having a second, opposite polarity is applied to the neural tissue. A DC having a third polarity that is the same as the first polarity can also be applied to the neural tissue to reduce the net charge delivered by the therapy delivery device. This configuration allows the total charge that can safely be delivered in the second phase to be as much as twice the charge in a typical pulse.

The current in any of the above embodiments can be applied to any suitable neural tissue in which signal transmission is desired to be blocked. For example, the neural tissue can be a component of the peripheral nervous system or the central nervous system. Regarding the peripheral nervous system, the neural tissue can be a peripheral nerve including cranial nerves, spinal nerves, motor efferent nerves, sensory afferent nerves, autonomic nerves, or any suitable combination thereof. The current can also be applied to collections of neurons, such as the brain, spinal cord or ganglia. The current can be applied to the axon, cell body or dendrites of a nerve so long as signal transmission is blocked and the neural tissue is not damaged.

Figure 13:
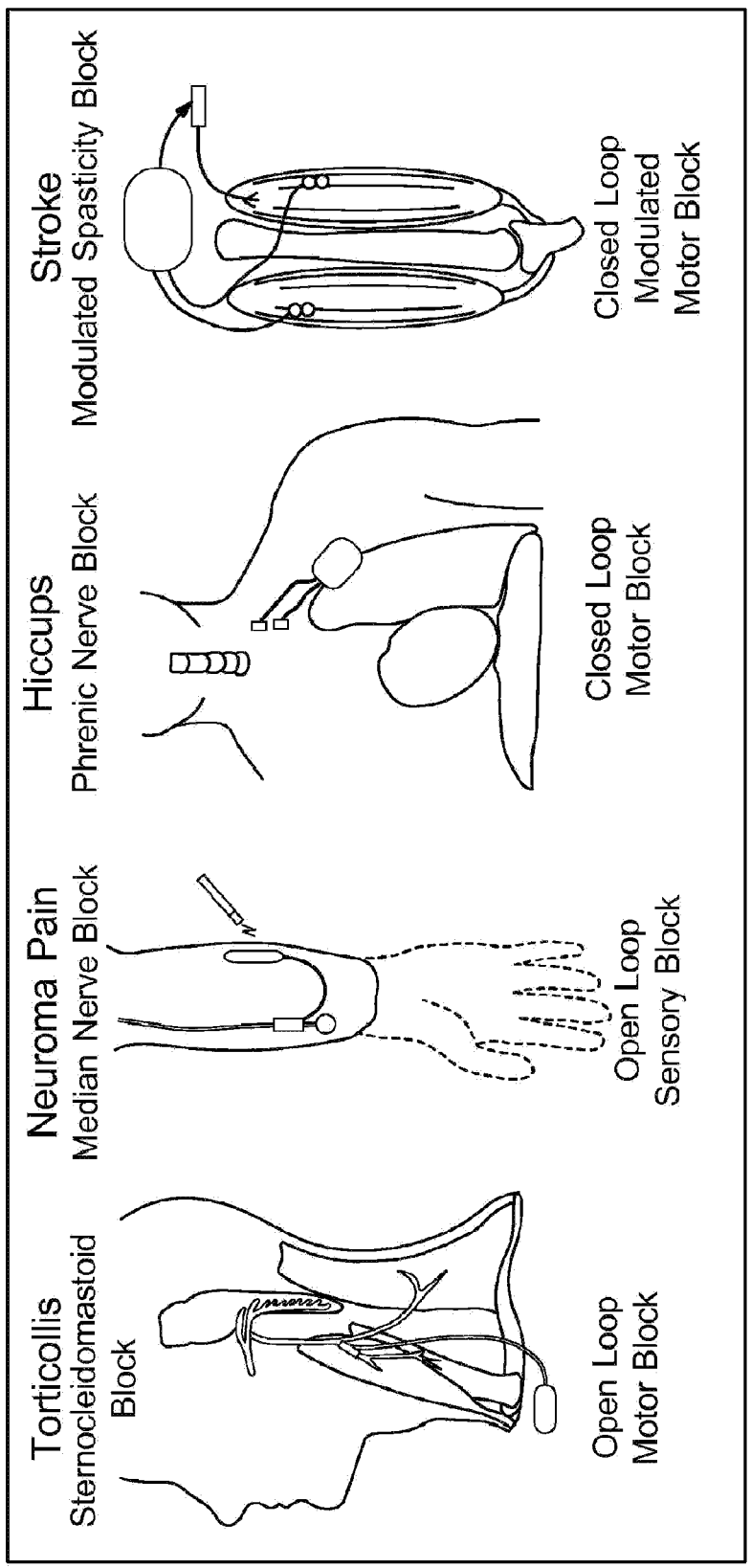
FIG. 13 is a schematic illustration of potential clinical applications for HFAC nerve conduction block. A block of muscle spasticity for dystonia, such as torticollis, can utilize one or more HFAC blocking electrode contacts on the motor branches to the targeted muscles to produce relaxation of the muscle(s). As a block for neuroma pain, the HFAC blocking electrode contact can be placed on the nerve proximal to the neuroma. In this application, the block is delivered continuously. Motor blocks that are triggered by a recorded signal include an application to block intractable hiccups. The impending hiccup is recorded as a large signal on the phrenic nerve and serves to trigger the HFAC block of the phrenic nerve to prevent diaphragm contraction for a brief period. Control of spastic muscles in stroke, multiple sclerosis and cerebral palsy is accomplished by recording the muscle signals from the spastic and non-spastic muscles to determine the intended movement of the user. A partial block of the spastic muscle can be delivered to allow voluntary control.

The methods can be used to affect abnormal function in patients. In particular, methods of the present invention can be used for motor nerve block, sensory nerve block, or autonomic block. In addition applications of methods of the present invention can be open loop, where control of block is through a switch, or closed loop, where block is controlled automatically via one or more physiological sensors. Exemplary clinical systems are depicted in FIG. 13.

Motor block applications include the block of muscle spasticity in stroke, cerebral palsy and multiple sclerosis. Such an application takes advantage of the gradability and quick reversibility of HFAC block. Function can restored with a partial block of motor activity, similar to the block produced by Botox or a phenol injection. In other cases, additional function can be provided by combining the HFAC block with an intelligent control system that varies the block based on sensed activity. For example, overpowering flexor spasticity often prevents stroke patients from voluntarily opening their hands By monitoring the myoelectric signal of the flexor and extensor muscles, the intention of the patient can be identified and the finger flexors can be partially blocked while activating the finger extensors with electrical stimulation when hand opening is desired.

In another embodiment, methods of the present invention are used to produce a relaxation of the urinary sphincter "on command." An example of an application where this is important is in electrical stimulation systems designed to produce bladder evacuation for individuals with spinal cord injury. In these systems, stimulation of the sacral roots produces bladder contraction for evacuation, but also produces unwanted sphincter contraction. The methods of the present invention can be applied bilaterally to the pudendal nerve to prevent sphincter activity during bladder activation. After the bladder is emptied, the block can be turned off to restore continence. The blocking electrode contact may also be used as stimulation to activate a weak sphincter and improve continence. Nerve conduction block on the sacral sensory roots can also be used to prevent spontaneous bladder contraction and thus improve continence. Methods can also be used to control bladder-sphincter dyssynergia in spinal cord injury.

Methods of the present invention can also be used as an alternative to neurolysis procedures to relieve contractures produced by muscle spasticity. For example, spastic ankle plantar flexors and hip adductors in cerebral palsy result in a characteristic pattern of contractures that limit function, make hygiene difficult and can become painful. Release of gastrocnemius tightness through tendon lengthening or neurolysis is usually only performed as a last resort due to the irreversible nature of these procedures. Since the HFAC block of methods of the present invention is reversible, it can be applied as a much earlier method of treatment. HFAC block could be applied throughout the night, or at specific times during the day, producing a period of complete relaxation of the gastrocnemius/soleus hip adductor muscles. During ambulation the block can be turned off, allowing patients to utilize the voluntary function of these muscles for walking. Early intervention may prevent the development of contractures in these muscles, eliminating the need for irreversible procedures.

Involuntary movements and spasticity that occur in conditions such as dystonias, choreas and tics can also be modulated by HFAC nerve block according to methods of the present invention. In many of these conditions, botulinum toxin injection has become a common treatment option. However, the need for repeated injections every few months is a significant disadvantage and can be quite expensive. Some cases appear to be resistant to treatment with botulinum toxin or become resistant after repeated treatments. At present, surgical alternatives are still utilized as a last resort in these cases. For these latter cases, HFAC block according to the present invention can provide a better treatment modality than irreversible surgical management and may be preferable to repeated botulinum toxin injections for some patients. An example of this type of application, torticollis, is shown in FIG. 13 and involves block of the sternocleidomastoid muscle and, in some cases, block of the posterior neck muscles.

Methods of the present invention can also be used to mitigate intractable hiccups where by blocking phrenic nerve conduction. The impending hiccup can be sensed through a nerve signal recording on the proximal phrenic nerve. A large volley of activity, indicating an impeding hiccup, can be used to trigger the HFAC block more distally on the phrenic nerve. In certain embodiments, the block is only applied for a very brief period in order to block the hiccup, and thus not interfering with normal breathing.

Regarding sensory nerve block applications, methods of the present invention can be used to block painful neuromas that develop following traumatic injury, such as limb amputation. Neuromas can be extremely painful, and the resulting disability can be significant and difficult to treat. Since the nerve end is transected (by amputation), the nerve no longer carries useful information. Therefore, a complete block of nerve activity is desirable.

HFAC blocks according to the present invention can be used for any painful conduction that is presently treated with neurolysis or chemical blocks, including cancer pain, post-herpetic neuralgia, and some cases of low back pain and headache. Some of these conditions are currently treated with peripheral nerve stimulation, which is not always effective and can produce a constant sensation due to the stimulation. With an HFAC block, a period of screening using a short acting local anesthetic applied to the nerve can be a prognosticator of HFAC success.

Regarding autonomic nerve block applications, destruction of specific components of the autonomic nervous system is utilized to treat certain conditions where no good alternative treatment exists. For example, destruction of the thoracic sympathetic ganglia is used to treat hyperhydrosis. Although this procedure can be successful, possible side-effects include Horner's Syndrome. The use of HFAC nerve block according to methods of the present invention at these sites allows the procedure to be performed in a reversible manner. The side effects may be able to be alleviated or reduced by activation of the autonomic block only when needed. In other embodiments, HFAC block is used for autonomic dysfunction including treatment for excessive drooling and treatment of pancreatic cancer pain (currently treated through destruction of the celiac plexus in extreme cases).

As such, methods of the present invention can be used to reduce spasticity in a patient suffering from cerebral palsy, stroke, or multiple sclerosis, for example, by blocking signal transmission through a nerve associated with the spasticity. The methods can be used to block muscle spasms in spinal cord injury or post-operatively after orthopaedic surgery to prevent involuntary contractions of the muscle. The methods can be used to block sensory signals, such as acute and chronic pain signals, in order to relieve pain. The methods can be used to block neural pain circuits in the spinal cord or brain in order to relieve chronic pain. The methods can be used to block tremors in Parkinson's Disease and related diseases by either blocking the peripheral nerves to the muscles or through block of the neural circuits in the brain. The methods can also be used to modulate the autonomic nervous system. Other indications include improving the symptoms of asthma in a patient suffering therefrom comprising blocking signal transmission through nerves generating the constriction of airways in asthma.

The present invention includes data using electrode contacts fabricated from high charge capacity ("Hi-Q") materials to achieve DC nerve block without damaging the nerve. In particular, in select examples, platinized Pt electrode contacts were used to achieve DC nerve block without damaging the nerve even after a large number (>100) of repeated applications. The high charge capacity materials result in a significant increase of the electrode contact's charge injection capacity, and are quantified in the Q value. In order to avoid nerve damage, the stored charge was retrieved after the blocking time by inverting the current drive and charge-balancing the Helmholtz Double Layer (HDL).

Figure 3A:
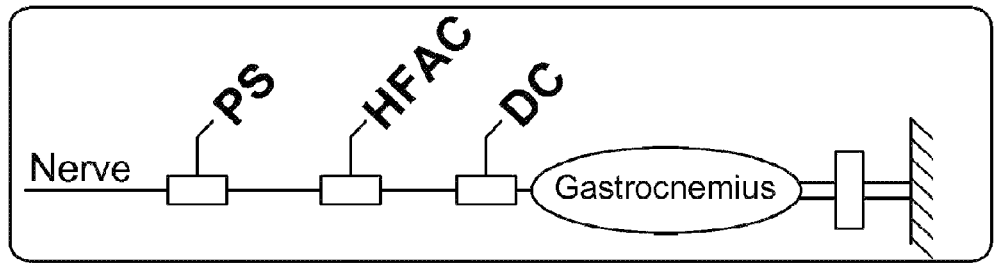
FIG. 3A is a schematic illustration of an electrode contact placed on a nerve. A gastrocnemius tendon is attached to a force transducer to measure force.
Figure 3B:
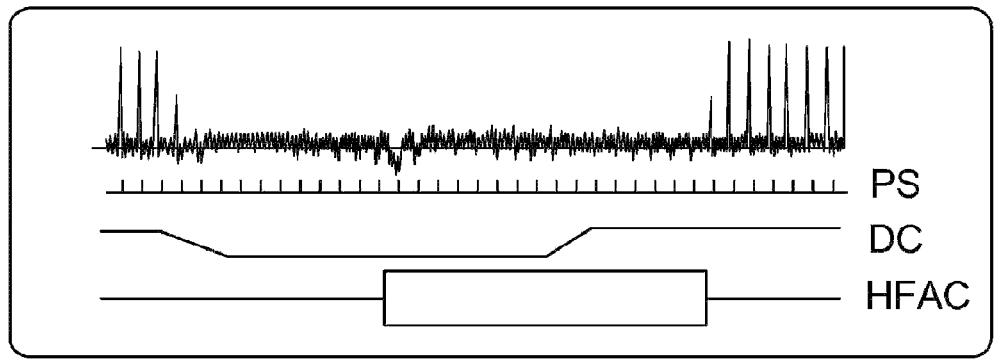
FIG. 3B is a graph depicting the no-onset block. The top trace shows tendon tension in Newtons during the trial. The proximal stimulation (PS) trace shows when the proximal stimulation occurs (once per second). Proximal stimulation (PS) at 2 Hertz (Hz) is delivered throughout the trial and the muscle twitches at the beginning of the trial each time the PS is delivered. DC ramps down (cathodic block) and plateaus at 4.5 seconds, producing complete block. At that point, PS is still delivered, but there is no muscle force. DC block allows HFAC to be turned on at 7.5 seconds without producing an onset response. DC is turned off and the block is maintained by the HFAC. HFAC is turned off at 17.5 second and normal conduction is restored.
Figure 3C:
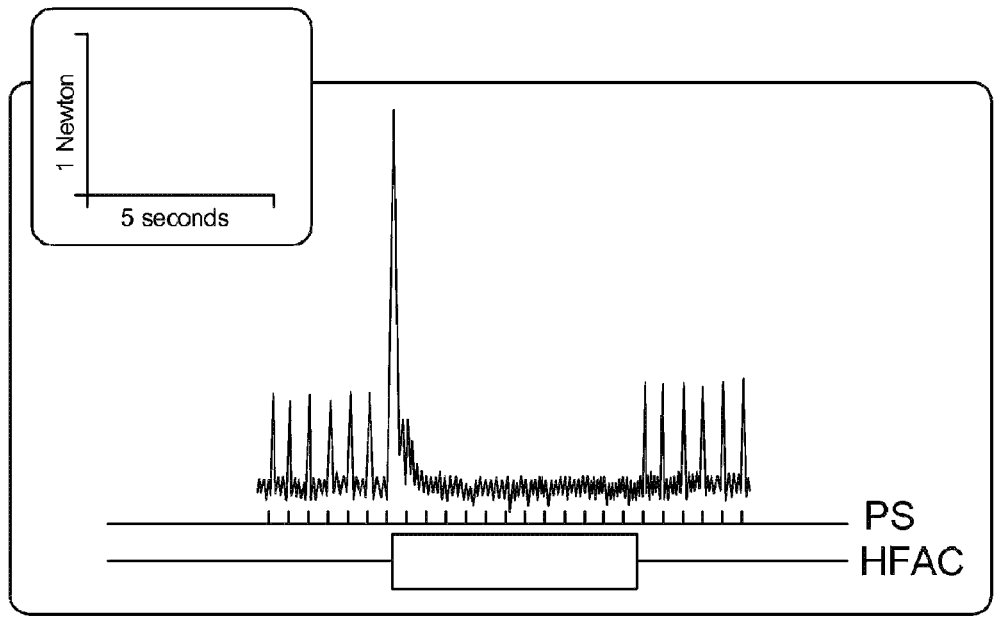
FIG. 3C is a graph depicting the normal HFAC onset (when DC block is not used).
Figure 4A:
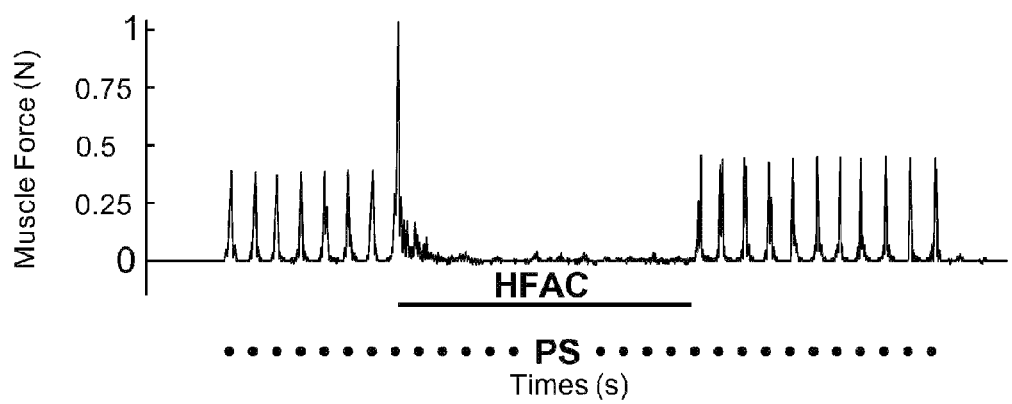
FIG. 4A is a graph illustrating that application of HFAC alone results in a large onset response before muscle activity is suppressed.
Figure 4B:
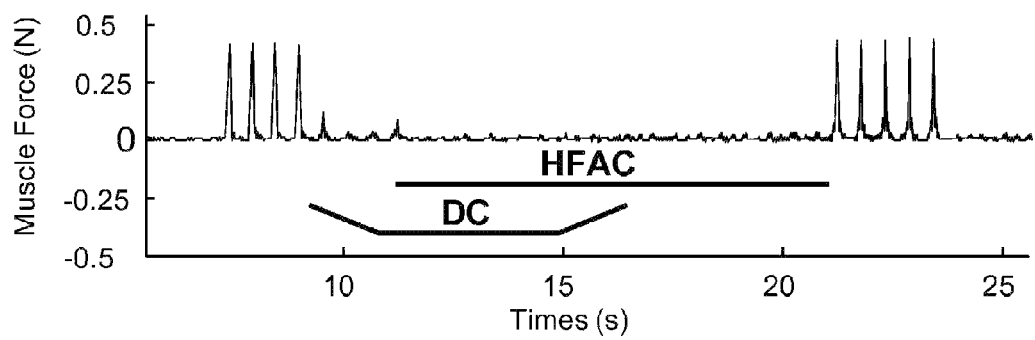
FIG. 4B is graph illustrating that a ramped DC waveform reduces the twitches evoked by PS and minimized the onset response caused by the HFAC waveform. The bar below the "HFAC" indicates when it is turned on. The bar under "DC" indicates when the DC is ramped from zero down to the blocking level and then back to zero again (zero DC is not shown).

Using a combination of Hi-Q DC electrode contacts and a HFAC electrode contact, successful no-onset block was demonstrated, as shown in FIG. 3. In experiments with this method, more than fifty successive block sessions without degrading nerve conduction was achieved. DC block (at 2.4 mA) was repeatedly applied over the course of approximately two hours for a cumulative DC delivery of 1500 seconds with no degradation in nerve conduction. FIG. 4 shows additional data depicting successful elimination of the onset response using the combination of HFAC and Hi-Q DC nerve block.

Figure 5:
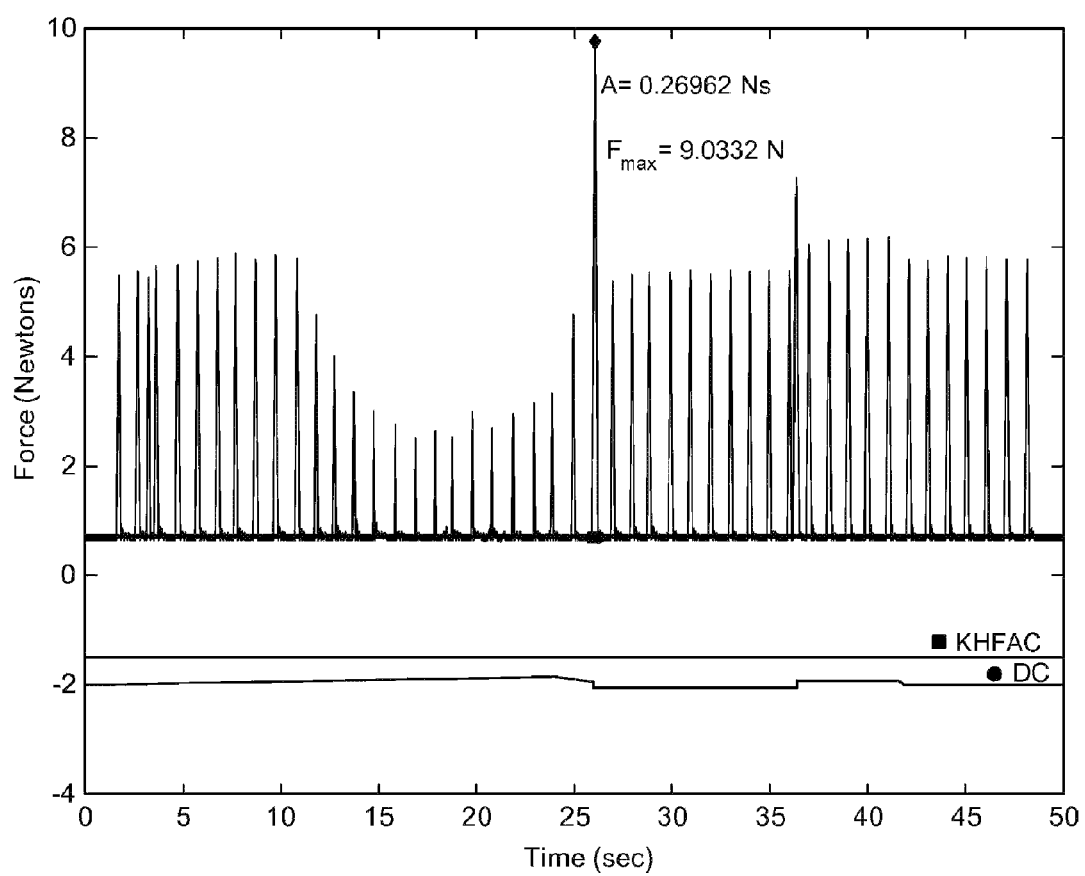
FIG. 5 is a graph illustrating the DC delivery with a pre-charge pulse, a blocking phase of opposite polarity and a final recharge phase. The pre-charge phase lasts 2 to 26 seconds, blocking phase of opposite polarity lasts 26-36 seconds, and a final recharge phase lasts for 36-42 seconds. The top trace shows that this waveform can be accomplished without producing significant unwanted activity in the nerve (nerve stimulated at 1 Hz). The results are from a rat sciatic nerve. "A" in FIG. 5 is the area under the curve for the spike and the $F_{max}$ is the peak force.

The use of a combined HFAC and Hi-Q DC nerve block requires that the DC can be delivered for a period of time sufficient to block the entire onset response of the HFAC. This typically lasts 1 to 10 seconds, and thus the DC should be delivered for that entire period. A method of further extending the total plateau time over which the DC can be safely delivered is to use a "pre-charge" pulse, as shown in FIG. 5. The pre-charge pulse comprises delivering a DC wave of opposite polarity from desired block effect for a length of time up to the maximum charge capacity of the electrode contact. The DC polarity is then reversed to produce the block effect. However, the block can now be delivered longer, potentially twice as long, because the electrode contact has been "pre-charged" to an opposite polarity. At the end of the prolonged block phase, the polarity is again reversed back to the same polarity as the pre-charge phase, and the total charge is reduced by delivery of this final phase. In most cases, the total net charge of this waveform will be zero, although beneficial effects can be obtained even if the total net charge is not completely balanced.

Figure 6A:
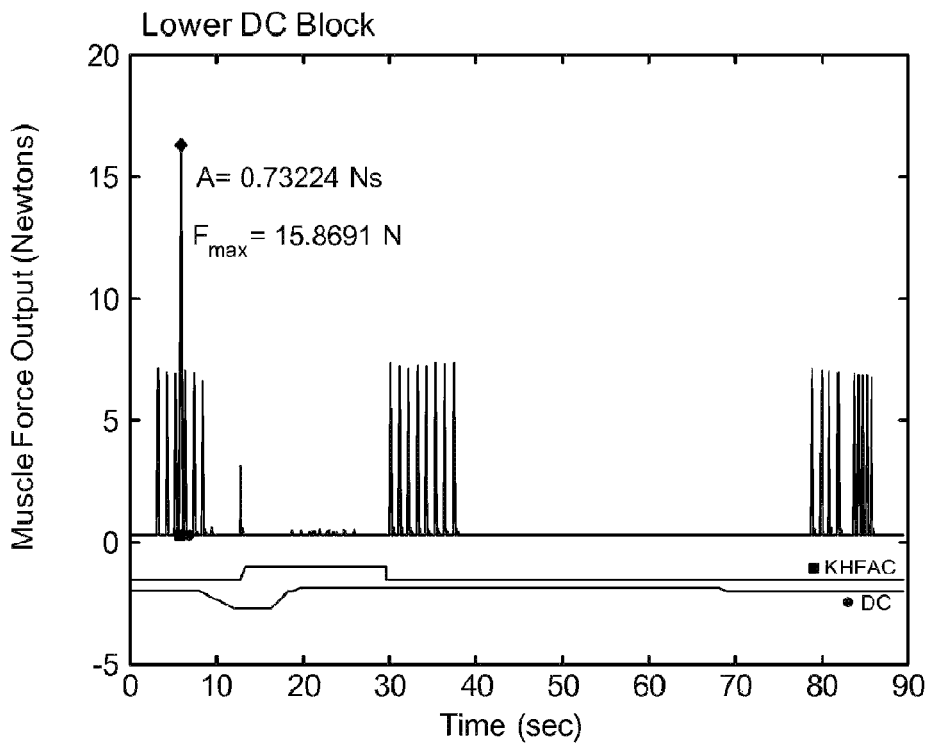
FIG. 6 is a graph showing that different amplitudes of DC block will block different percentages of the HFAC onset response. The onset response compared in FIG. 6A
FIG. 6B is the single spike that occurs at about 12 seconds in FIG. 6A and at about 16 seconds in FIG. 6B.
Figure 6B:
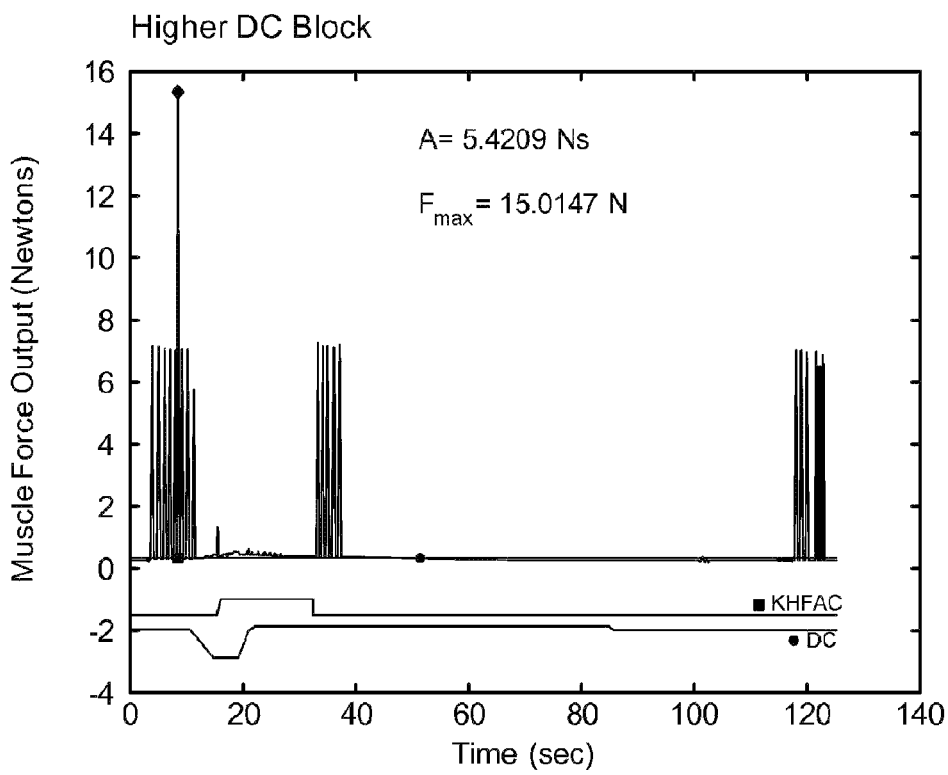

Varying the level of DC can partially or fully block the onset response from the HFAC, as shown in FIG. 6. This can be useful to assess the nerve health by verifying a small response even in the midst of significant nerve block. The depth of the DC block can be assessed through this method.

Figure 7A:
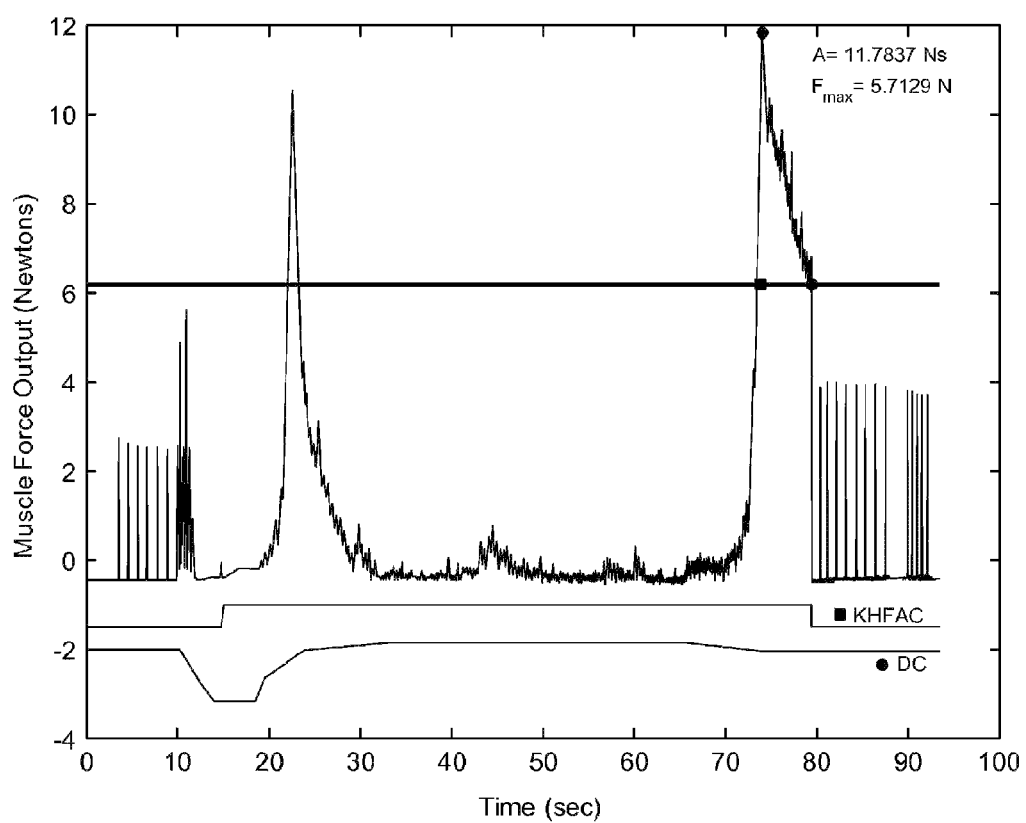
FIGS. 7A and 7B are graph illustrating the use of different slopes and multiple transitions in the DC waveform to avoid activating a muscle as the current level is varied. With steeper slopes between transitions, significant activity is induced in the nerve. This activity can be reduced or eliminated by reducing the slope of the transitions in the DC waveform. The two lowers traces show when HFAC and DC are on. HFAC and DC are at zero when the trial starts (0 seconds).
Figure 7B:
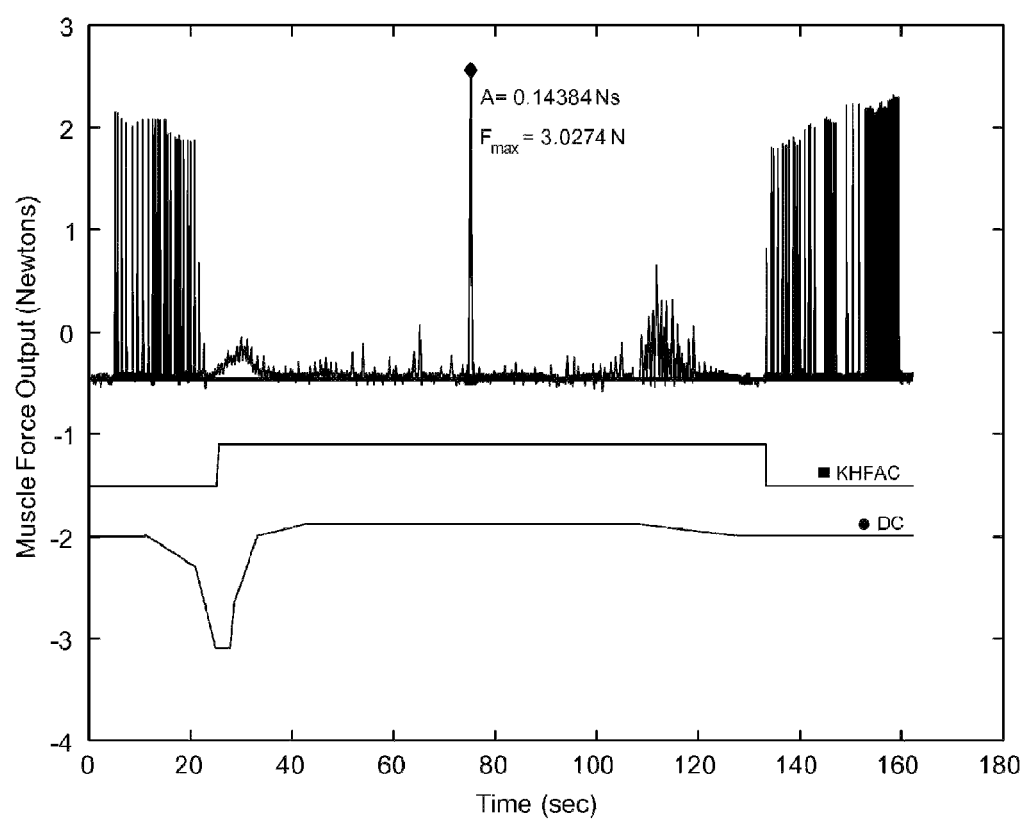

Multi-Slope transitions may help avoid onset response, especially with discrete changes in DC-current-amplitude over time (slope) in a real-world device. This is shown in FIG. 7, which are results from a rat's sciatic nerve. In these examples, the DC begins with a low slope to prevent firing of the nerve at low amplitudes. The slope can then be increased to reach the blocking amplitude quicker. Once DC block amplitude has been achieved, block is maintained for the duration required to block the HFAC onset response. The HFAC is turned on once the DC has reached blocking plateau. The HFAC is turned on at the amplitude necessary to block. Once the onset response has completed, the DC is reduced, initially rapidly and then more slowly in order to prevent activation of the nerve. The DC is then slowly transitioned to the recharge phase where the total charge injection is reduced. In this example, the recharge phase is at a low amplitude and lasts for over 100 seconds. HFAC block can be maintained throughout this period and can then be continued beyond the end of the DC delivery if continued nerve block is desired. Once the total period of desired block has been completed (which could be many hours in some cases), the HFAC can be turned off and the nerve allowed to return to normal conducting condition. This process can be repeated again and again as needed to produce nerve block on command as desired to treat disease.

Figure 8:
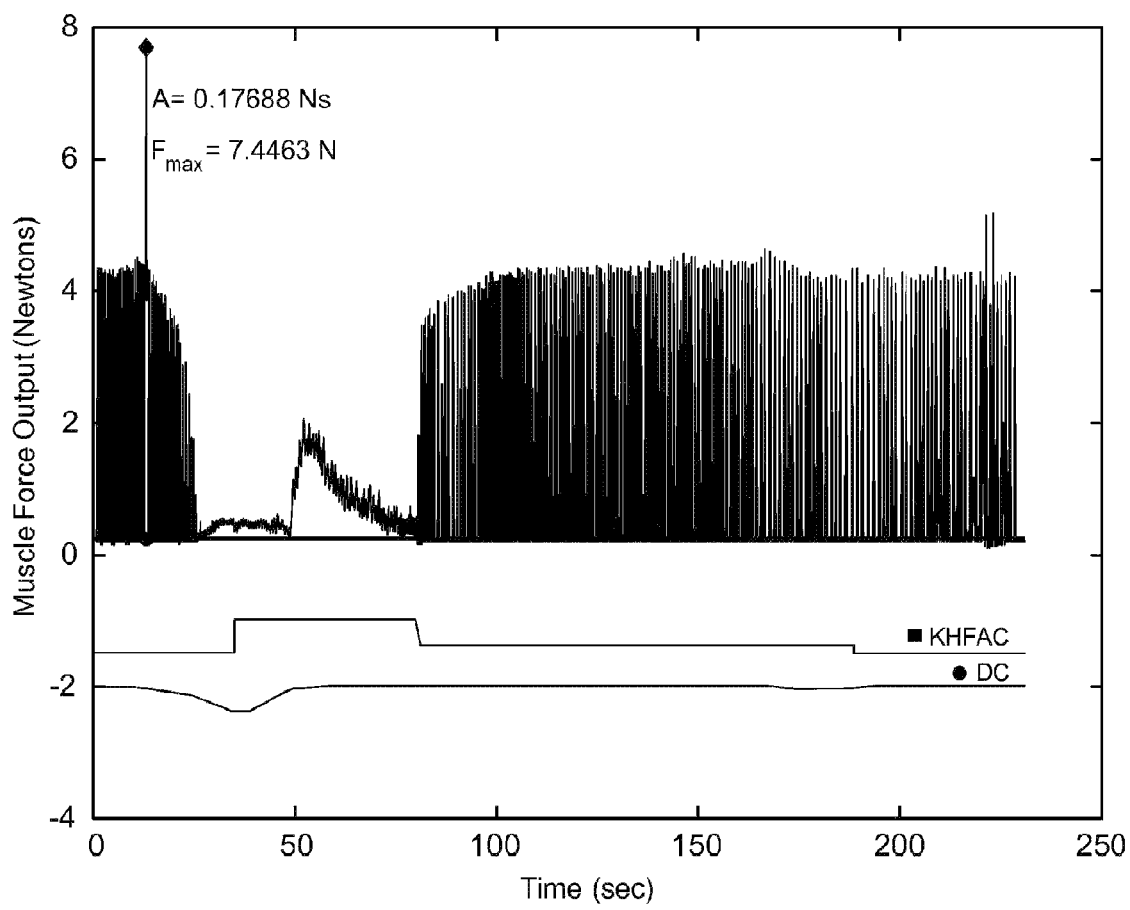
FIG. 8 is a graph showing a DC block that is too short to block the entire HFAC onset response. The two lowers traces show when HFAC and DC are on. HFAC and DC are at zero when the trial starts (0 seconds).

FIG. 8 shows that the DC is maintained throughout the period of the onset response from the HFAC in order to block the entire onset response. In this example (rat sciatic nerve), the onset response lasts about 30 seconds. The DC waveform (blue trace) initially blocks the onset response, but when the DC ramps back to zero, the onset response becomes apparent (at ~50 seconds). This illustrates very long DC blocking waveforms to combine the HFAC and DC blocks to achieve a no-onset block.

According to another example, monopolar nerve cuff electrode contacts were manufactured using platinum foil. These electrode contacts were then platinized in chloroplatinic acid solutions to create platinum black coatings of various roughness factors from 50 to over 600. A cyclic voltammogram for each of the electrode contacts was generated to determine the water window. The amount of charge that could be safely delivered by these electrode contacts (the "Q value") was estimated by calculating the charge associated with hydrogen adsorption from −0.25V to +0.1V vs. a standard Ag/AgCl electrode contact.

Figure 9:
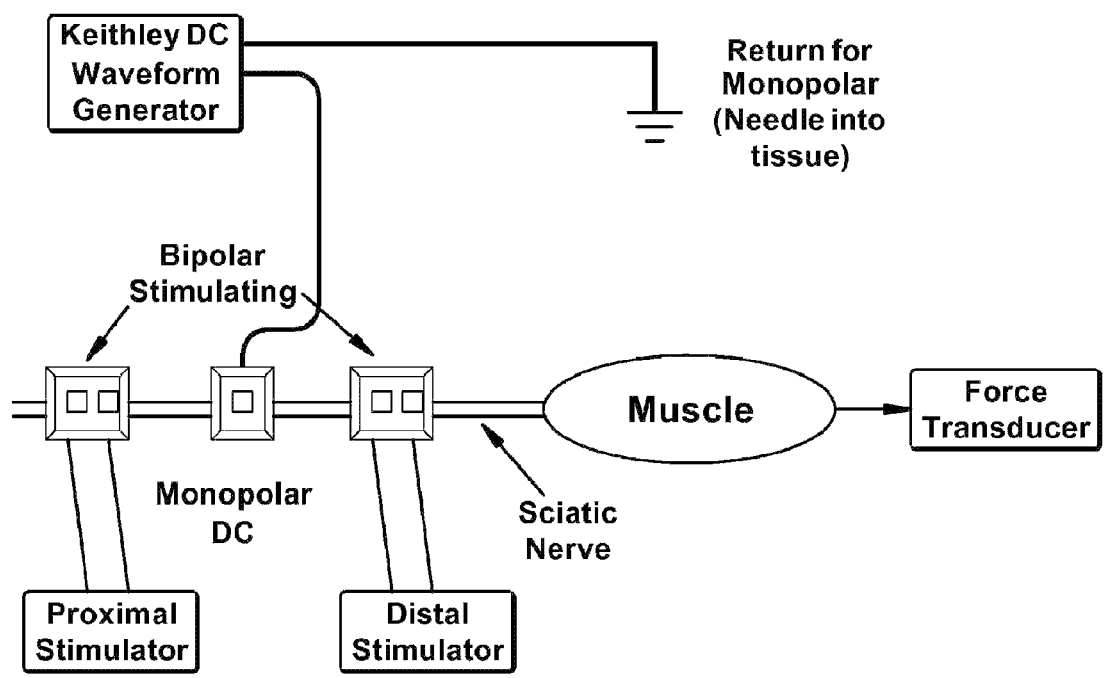
FIG. 9 is a diagram depicting one example of a system for using DC to block nerve signal transmission without damaging the nerve according to an embodiment of the present invention.

Acute experiments were performed on Sprague-Dawley rats to test the efficacy of DC nerve block with these electrode contacts. Under anaesthesia, the sciatic nerve and the gastrocnemius muscle on one side was dissected. Bipolar stimulating electrode contacts were placed proximally and distally on the sciatic nerve. The proximal stimulation (PS) elicited muscle twitches and allowed the quantification of motor nerve block. The distal stimulation (DS) also elicited muscle twitches and these twitches were compared with those from PS as a measure of nerve damage under the DC electrode contact. A monopolar electrode contact was placed between the two stimulating electrode contacts as schematically illustrated in FIG. 9. Both platinum and platinum black electrode contacts were tested in this location.

DC experiments were performed in rats to determine the effect of DC pulses of various current levels and durations. A current-controlled waveform generator (Keithley Instruments, Solon, Ohio) was used to create the DC waveform. The waveform was a trapezoidal blocking phase followed by a square recharge phase as depicted in the lower graph of FIG. 10. The ramp up and down ensured that there was no onset firing from the DC. The DC parameters were chosen so that the total charge delivered was less than the Q value for a given electrode contact. Each cathodic (blocking) pulse was then followed by a recharge phase in which 100% of the charge was returned to the electrode contact by an anodic pulse maintained at 100 µA.

Figure 11:
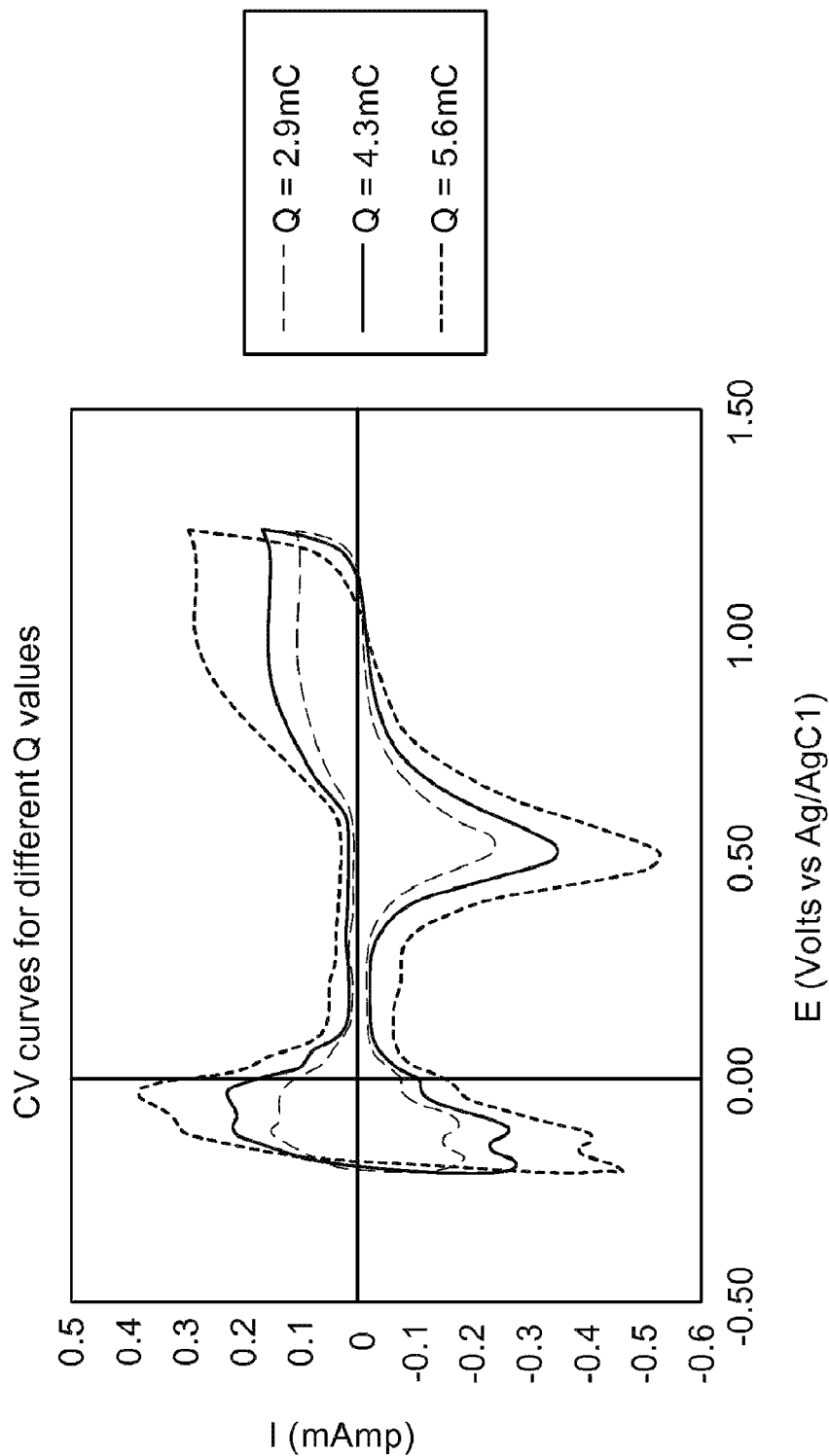
FIG. 11 is a cyclic voltammogram of several electrode contacts with different Q values.

The cyclic voltammogram for several of these electrode contacts in 0.1M $H_2SO_4$ is shown in FIG. 11. Typically Q values for these electrode contacts ranged from 2.9 mC to 5.6 mC. In contrast, a standard Pt foil electrode contact has a Q value of 0.035 mC.

Platinum black electrode contacts were successfully used to achieve a conduction block while maintaining the total charge below the maximum Q value for each electrode contact. FIG. 10 illustrates a trial where complete motor nerve block was obtained using DC with a peak amplitude of 0.55 mA. The muscle twitches elicited by PS were completely blocked during the plateau phase of the DC delivery.

Figure 12:
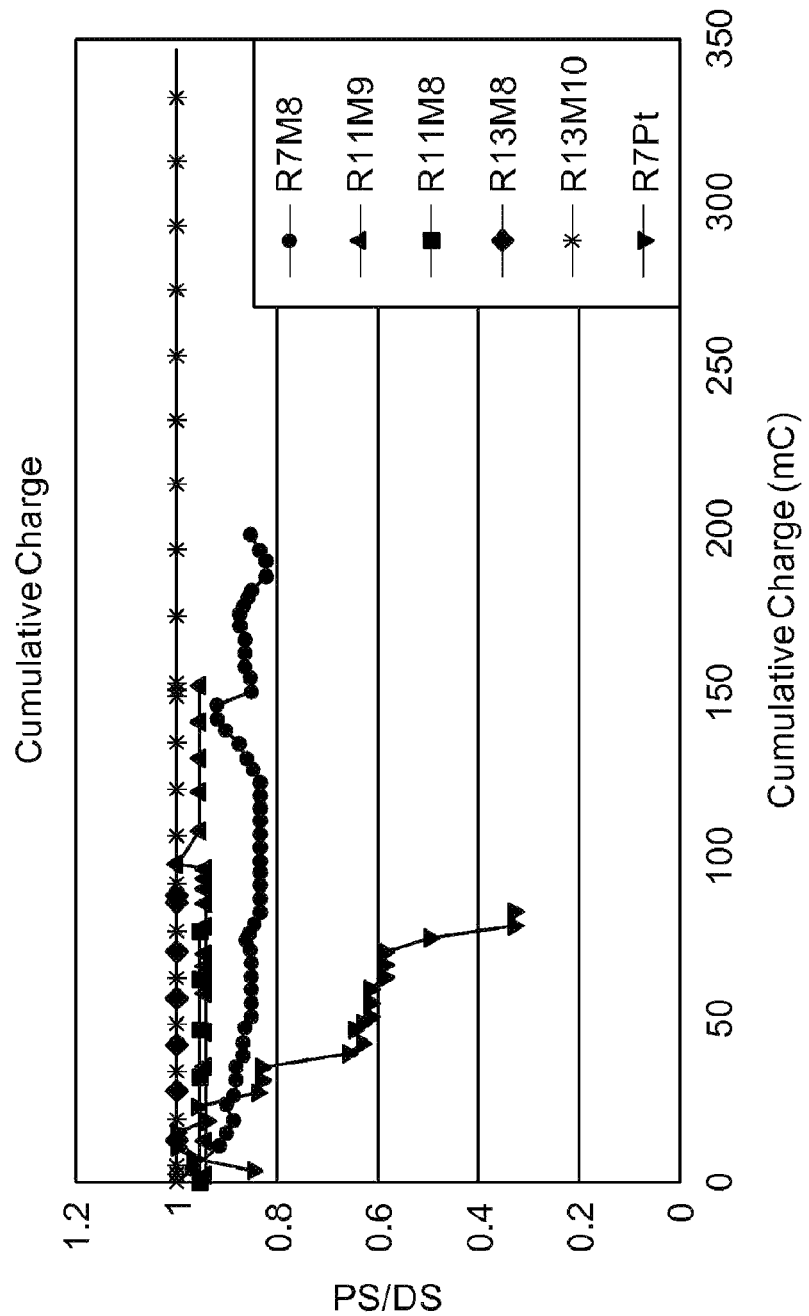
FIG. 12 is a graph depicting the viability of sciatic nerve conduction following nerve block with DC (PS/DS is the muscle force ratio, which is used as an output measure to determine acute nerve damage).

FIG. 12 illustrates the effects of cumulative dosages of DC for five of the platinum black electrode contacts as compared to a standard platinum electrode contact. DC was delivered as shown in FIG. 10 (lower subplot). Each cycle of DC was followed by PS and DS to produce a few twitches (not shown in FIG. 10). The PS/DS ratio is a measure of acute nerve damage. If the nerve is conducting normally through the region under the block electrode contact, the ratio should be near one. The platinum electrode contact demonstrated nerve damage in less than one minute after delivery of less than 50 mC and the nerve did not recover in the following 30 minutes. The platinum black electrode contacts do not show signs of significant neural damage for the duration of each experiment, up to a maximum of 350 mC of cumulative charge delivery. Similar results were obtained in repeated experiments using other platinum black electrode contacts with variable Q values.

The foregoing description and examples have been set forth merely to illustrate the invention and are not intended as being limiting. Each of the disclosed aspects and embodiments of the present invention may be considered individually or in combination with other aspects, embodiments, and variations of the invention. Further, while certain features of embodiments of the present invention may be shown in only certain figures, such features can be incorporated into other embodiments shown in other figures while remaining within the scope of the present invention. In addition, unless otherwise specified, none of the steps of the methods of the present invention are confined to any particular order of performance. Modifications of the disclosed embodiments incorporating the spirit and substance of the invention may occur to persons skilled in the art and such modifications are within the scope of the present invention. Furthermore, all references cited herein are incorporated by reference in their entirety.

The invention claimed is:

1. A therapy delivery device comprising:
   an electrode contact adapted to directly contact a nerve,
   wherein the electrode contact comprises a high charge capacity material that prevents formation of irreversible electrochemical reaction products when a charge of 100 µC or more is delivered to the nerve by the electrode contact, and
   the electrode contact having a geometric surface area of at least about 1 $mm^2$.

2. The therapy delivery device of claim 1, wherein the geometric surface area is between about 3 $mm^2$ and 9 $mm^2$.

3. The therapy delivery device of claim 1, wherein the electrode contact is fabricated of the high charge capacity material or the electrode contact comprises a base body at least partially coated with the high charge capacity material.

4. The therapy delivery device of claim 1, wherein the high charge capacity material is platinum black, titanium nitride, tantalum, or poly(ethylenedioxythiophene).

5. The therapy delivery device of claim 1, wherein the therapy delivery device is a nerve cuff.

6. The therapy delivery device of claim 5, wherein the electrode contact comprises a plurality of electrode contacts.

7. The therapy delivery device of claim 1, wherein the electrode contact comprises a plurality of monopolar nerve cuff electrode contacts.

8. A system comprising:
- a waveform generator to generate a direct current (DC) with a total amount of charge of 100 microcoulombs or more;
- an electrical contact, coupled to the waveform generator, adapted to be placed into direct contact with a nerve to deliver the DC to the neural tissue without producing irreversible reaction products that damage the nerve,
- wherein the electrical contact is fabricated from a high charge-capacity material that prevents formation of irreversible electrochemical reaction products when a charge of 100 µC or more is delivered to the nerve by the electrode contact, and
- wherein the electrode contact having a geometric surface area of at least about 1 $mm^2$.

* * * * *